United States Patent [19]

Whitney et al.

[11] 4,172,833

[45] Oct. 30, 1979

[54] PROCESS FOR PREPARATION OF 2-MERCAPTOTOLUIMIDAZOLE AND SALTS THEREOF

[75] Inventors: Thomas G. Whitney, Westport; Lester A. Doe, Jr., Newtown; Harry E. Hill, Wallingford, all of Conn.

[73] Assignee: R. T. Vanderbilt Company, Inc., Norwalk, Conn.

[21] Appl. No.: 888,269

[22] Filed: Mar. 20, 1978

[51] Int. Cl.² ............................................. C07D 235/28
[52] U.S. Cl. ..................................... 548/105; 548/305
[58] Field of Search ......................... 548/305; 260/299

[56] References Cited

U.S. PATENT DOCUMENTS

| | | | |
|---|---|---|---|
| 1,973,724 | 9/1934 | Perkins et al. | 260/575 |
| 2,642,396 | 6/1953 | Roddy, Jr. | 548/305 |
| 2,894,034 | 7/1959 | Shull | 260/578 |
| 2,901,513 | 8/1959 | Thomas | 260/584 |
| 2,964,561 | 12/1960 | Normington et al. | 260/578 |
| 3,068,289 | 12/1962 | Woodbridge | 260/578 |
| 3,154,583 | 10/1964 | Dombrow et al. | 260/578 |
| 3,842,098 | 10/1974 | Scherhag | 548/305 |
| 3,883,546 | 5/1975 | Sutton et al. | 260/299 |
| 3,895,025 | 7/1975 | Goodman | 548/305 |
| 4,011,194 | 3/1977 | Sandler | 260/299 |

OTHER PUBLICATIONS

Van Allan et al., Organic Syntheses, vol. IV, 1963, N.Y., Wiley, pp. 569-570.
Audrieth et al., The Chemistry of Hydrazine, 1951, pp. 224-227.

*Primary Examiner*—Alan L. Rotman
*Assistant Examiner*—Natalia Harkaway
*Attorney, Agent, or Firm*—Rasma B. Balodis

[57] ABSTRACT

Process for the production of 2-mercaptotoluimidazole by reacting stabilized o-toluenediamine with carbon disulfide in a solvent and recovering the formed product by filtration. o-Toluenediamine is stabilized with hydrazine or its salts. Subsequently 2-mercaptotoluimidazole is converted to a metal salt.

5 Claims, No Drawings

PROCESS FOR PREPARATION OF 2-MERCAPTOTOLUIMIDAZOLE AND SALTS THEREOF

BACKGROUND OF THE INVENTION

1. Field of the Invention

This invention relates to a process for the production of high purity, light color 2-mercaptotoluimidazole and metal salts thereof in high yields.

2. Description of the Prior Art

It is known that 2-mercaptotoluimidazole can be obtained by reaction of o-toluenediamine with carbon disulfide in a solvent. The reaction is accelerated by the addition of catalytic quantities of alkali metal hydroxides or tertiary amines. However, the product thus obtained is discolored and contains impurities which are difficult to remove by subsequent purification processes. The poor quality of the product is caused by the use of discolored o-toluenediamine as a starting material. o-Toluenediamine is highly susceptible to discoloration upon exposure to air, heat, light, moisture and the like. As a result, autooxidation products are formed almost immediately after preparation of the amine. In the preparation of 2-mercaptotoluimidazole, the autooxidation products are coprecipitated as impurities thus causing discoloration and further deterioration of the imidazole. For applications where light color 2-mercaptotoluimidazole is desired, high purity o-toluenediamine must be used as a starting material. This can be achieved by distillation of the amine and immediate use thereafter. However, in practical application, it is not always possible to combine the distillation step with production. Another suggested approach is storage of the amine under an inert gas at positive pressures. However, the treatment is of temporary nature and upon further handling or processing, the stability is easily lost. Special equipment and handling techniques are required which are often inconvenient for large scale operations.

Toluenediamines have been also stabilized by addition of stabilizers. Thus, U.S. Pat. No. 2,894,034 discloses the addition of elemental sulfur. However, in the preparation of 2-mercaptotoluimidazole, sulfur coprecipitates and it is necessary to remove the stabilizer from the final product by recrystallization or other purification methods. It has now been discovered that 2-mercaptotoluimidazole of high purity and light color can be prepared by using a stabilized raw material system without a separate stabilizer removal step.

SUMMARY OF THE INVENTION

According to the invention, a process for producing high purity 2-mercaptotoluimidazole has been discovered which comprises reacting stabilized raw material system comprising o-toluenediamine and a stabilizer selected from the group consisting of hydrazine, hydrazine hydrate, and hydrazine salts of strong acids and carbon disulfide in a solvent, collecting the formed 2-mercaptotoluimidazole by filtration and recovering the solvent for recycling. According to another aspect of the invention, the formed 2-mercaptotoluimidazole is converted to a metal complex by addition of the corresponding metal salt.

DETAILED DESCRIPTION OF THE INVENTION

According to the invention, high purity 2-mercaptotoluimidazole is prepared by reacting o-toluenediamine and an equimolar amount of carbon disulfide in an organic alcoholic solvent by the following reaction scheme:

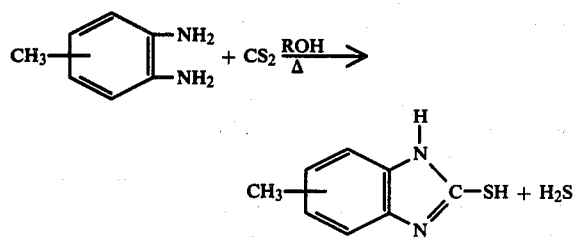

The solvent is selected from organic alcohols of the formula ROH wherein R is alkyl. Especially preferred are lower aliphatic alcohols having 1–6 carbons in the alkyl group. The o-toluenediamine may be a single isomer or a mixture of isomers. A preferred starting material is commercial o-toluenediamine which is usually provided in the form of mixed isomers. A typical commercial product contains about 30 to 50 percent by weight of the 2,3-isomer and 50 to 70 percent by weight of the 3,4-isomer. The material may further contain meta- and para-isomers. Naturally, where an isomeric mixture of ortho-amines is used as the starting material, the reaction product will be a corresponding isomeric mixture. For the purposes of the invention, it will be understood that either o-toluenediamine containing only one isomer or mixtures thereof may be used.

It is critical to the invention that high purity o-toluenediamine is used. However, freshly distilled o-toluenediamine rapidly becomes autooxidized due to exposure to oxygen, light and heat, and must be used rapidly before color degradation takes place. According to the invention, a more convenient alternative is to stabilize o-toluenediamine against color degradation by adding about 0.025 to 2.0 percent by weight and preferably 0.1 to 0.5 percent by weight of a stabilizer selected from the group consisting of hydrazine, hydrazine hydrate and hydrazine salts of strong acids. Especially preferred are hydrazine sulfate and hydrazine hydrochloride. In the case of freshly distilled amine, at least 0.025 percent and preferably 0.1 percent of stabilizer is sufficient to prevent discoloration. If stabilizer is not added and autooxidation has already set in, up to 2.0 percent stabilizer may be required to prevent further discoloration.

The use of stabilized o-toluenediamine affords several advantages over prior art processes:

(1) The product, 2-mercaptotoluimidazole is of high purity, and white or off-white in color. Thus, no subsequent purification is necessary for most applications. For example, the imidazole can be used as antioxidant in light colored polymers without adverse effects on the color.

(2) Build-up of contamination from impure commercial amine is eliminated and the reaction solvent can be recycled in continuous operation or reused in batch operation without purification. As a result, there is no loss of the imidazole due to incomplete product recovery as well as improved solvent economy.

(3) The process does not require any catalysts and therefore catalyst separation steps are not necessary.

The 2-mercaptotoluimidazole can be converted to a metal salt in situ by adjusting pH to 8.5 to 11 with a base and adding an inorganic metal salt. The metal salts may be selected from oxides, halides, and sulfates of group IIB and IVB metals and alkaline earth metals.

The following examples are submitted to further illustrate, but not to limit the scope of the invention. Unless otherwise indicated, all parts and percentages in the specification and claims are based upon weight.

EXAMPLE I

In a start-up operation, a 500 ml three-neck reaction flask equipped with a reflux condenser under stirring was charged with 150 grams of anhydrous isopropanol and 50 grams of o-toluenediamine containing 0.5 percent hydrazine stabilizer. The o-toluenediamine was a highly purified mixture of 2,3- and 3,4- isomers. After the diamine has dissolved, 42 grams of carbon disulfide are added at 20°-30° C. and the reaction mixture is stirred for two hours at 25° C. and then refluxed until no hydrogen sulfide evolution is noted. After cooling to room temperature, the formed 2-mercaptotoluimidazole is filtered, washed with small amounts of fresh isopropanol and dried at 50° C. The product is a white powder with a brightness rating of 78 as determined by the TAPPI standard T-452M-58 method. The yield is 45 grams (67 percent). Approximately 20 grams of the product remains dissolved in the solvent. The solvent is saved for recycling in subsequent runs of the process.

EXAMPLE II

The solvent of the start-up run described in Example I is adjusted to 150 g and used for preparation of a second batch of 2-mercaptotoluimidazole by the method described hereinabove. The product is white in color with a brightness rating of 87. The yield is 98 percent. Due to the reuse of the solvent, there is no overall loss of the product and high yields can be obtained without detrimental effect on the color of the product. As before, the solvent can be reused in subsequent batch operations.

EXAMPLE III

The solvent from Example II is adjusted to 150 g and is used for preparation of a third batch of 2-mercaptotoluimidazole by the method described in Example I. Instead of filtering, 2-mercaptotoluimidazole is converted in situ to the zinc salt by adding to the alcohol-imidazole mixture 16.7 grams zinc oxide and 4 grams ammonium hydroxide and refluxing for four hours. After cooling to 20°-30° C., 150 grams water is added and the product is filtered off. The product is white in appearance and the yield is 95%.

EXAMPLE IV

Accelerated storage tests were conducted to demonstrate the color stability of 2-mercaptotoluimidazole prepared by the use of stabilized raw material systems according to the invention. Freshly distilled o-toluenediamine containing no stabilizer and distilled o-toluenediamine containing 0.5 percent stabilizer of the invention was stored for 33 hours at 100° C. Subsequently, the stored diamines, a freshly distilled and a commercial o-toluenediamine were converted to 2-mercaptotoluimidazole and tested for brightness according to the method described in Example I. The results are compiled in Table I.

TABLE I

| Starting Material o-toluenediamine | Stabilizer | Storage Time, Hrs. | Brightness of 2-mercaptotoluimidazole |
|---|---|---|---|
| commercial grade | none | 0 | 43 |
| distilled | none | 0 | 75 |
| distilled | none | 33 | 65 |
| distilled | hydrazine sulfate | 33 | 81 |
| distilled | hydrazine hydrochloride | 33 | 73 |

The results demonstrate that the use of a stabilized o-toluene even after storage under severely detrimental conditions result in high quality products of superior color. While immediate use of freshly distilled diamine results in satisfactory products, storage for any length of time without the protection of stabilizer results in deterioration of the quality of the 2-mercaptotoluimidazole.

While certain representative embodiments have been shown for the purpose of illustrating the invention, it will be apparent to those skilled in the art that certain variations and modifications may be made therein without departing from the true scope of the invention.

We claim:
1. A process for the production of light colored 2-mercaptotoluimidazole which comprises the steps of:
    (1) adding to o-toluenediamine about 0.025 to 2.0 percent by weight of a stabilizer selected from the group consisting of hydrazine, hydrazine hydrate, and hydrazine salts of strong acids;
    (2) dissolving said diamine in alcoholic solvent;
    (3) adding carbon disulfide at about 20° to 35° C.;
    (4) refluxing the resulting reaction mixture until all hydrogen sulfide is evolved;
    (5) cooling the mixture;
    (6) separating the produced 2-mercaptotoluimidazole from the solvent.
2. A process according to claim 1 in which the solvent is alkyl alcohol having 1-6 carbons in the alkyl radical.
3. A process according to claim 1 where the hydrazine salts of strong acids are selected from the group consisting of hydrazine sulfate and hydrazine hydrochloride.
4. A process according to claim 1 where the solvent is recycled.
5. A process for the production of light colored metal salt of 2-mercaptotoluimidazole which comprises the steps of:
    (1) adding to o-toluenediamine about 0.025 to 2.0 percent by weight of a stabilizer selected from the group consisting of hydrazine, hydrazine hydrate, and hydrazine salts of strong acids;
    (2) dissolving said diamine in alcoholic solvent;
    (3) adding carbon disulfide at about 20° to 35° C.;
    (4) refluxing the resulting reaction mixture until all hydrogen sulfide is evolved;
    (5) adding (a) inorganic metal compound selected from the group consisting of oxides, halides, and sulfates of group IIB and IVB metals and alkaline earth metals and (b) a base to the reaction mixture;
    (6) refluxing;
    (7) cooling the mixture;
    (8) adding water;
    (9) separating the formed metal salt of 2-mercaptotoluimidazole from the solvent.

* * * * *